United States Patent [19]

Schneider et al.

[11] Patent Number: 5,525,728

[45] Date of Patent: Jun. 11, 1996

[54] PROCESS FOR THE PRODUCTION OF SCLAREOLIDE

[75] Inventors: Markus Schneider, Duisburg; Theo Stalberg, Monheim; Thomas Gerke, Neuss, all of Germany

[73] Assignee: Henkel Kommanditgesellschaft auf Aktien, Duesseldorf, Germany

[21] Appl. No.: 318,790

[22] PCT Filed: Apr. 8, 1993

[86] PCT No.: PCT/EP93/00874

§ 371 Date: Oct. 17, 1994

§ 102(e) Date: Oct. 17, 1994

[87] PCT Pub. No.: WO93/21174

PCT Pub. Date: Oct. 28, 1993

[30] Foreign Application Priority Data

Apr. 16, 1992 [DE] Germany ............ 42 12 731.9

[51] Int. Cl.⁶ .................................. C07D 307/92
[52] U.S. Cl. ........................... 549/299; 562/467
[58] Field of Search ................................ 549/299

[56] References Cited

U.S. PATENT DOCUMENTS

| | | | |
|---|---|---|---|
| 3,050,532 | 8/1962 | Schumacher et al. | 260/343.3 |
| 4,503,240 | 3/1985 | Staiger et al. | 549/299 |
| 5,212,078 | 5/1993 | Farbood et al. | 549/299 |
| 5,247,100 | 9/1993 | Gerke et al. | 549/299 |
| 5,290,955 | 3/1994 | Asanuma et al. | 549/299 |

FOREIGN PATENT DOCUMENTS

| | | |
|---|---|---|
| 2676229 | 11/1992 | France . |
| 3942358 | 6/1991 | Germany . |

OTHER PUBLICATIONS

Ullmanns Enzyklopädie der technischen Chemie, vol. 20, p. 283, Weinheim 1981.

*Primary Examiner*—Joseph E. Evans
*Attorney, Agent, or Firm*—Wayne C. Jaeschke; John E. Drach; Henry E. Millson, Jr.

[57] ABSTRACT

A process for the production of sclareolide comprising the steps of: (1) providing an aqueous composition comprised of: (a) water; (b) sclareol, abienol, or a mixture of sclareol and abienol, (c) an effective amount of a ruthenium catalyst; and, (d) an emulsifying agent; (2) forming an aqueous alkaline composition by adding an alkali metal hydroxide to said aqueous composition; (3) reacting said aqueous alkaline composition with an oxidizing agent to form a crude product; and either: (4) further reacting said crude product with base to form the salt of 8α-hydroxy-11-carboxyl-12, 13, 14, 15, 16-pentanorlabdane and; (5) reacting said salt with acid to form sclareolide;

or: (4) heating said crude product to form sclareolide.

20 Claims, No Drawings

[5,525,728]

PROCESS FOR THE PRODUCTION OF SCLAREOLIDE

This application is a 371 of PCT/EP93/00874 filed Apr. 8, 1993.

BACKGROUND OF THE INVENTION

1. Field of the Invention

This invention relates to a process for the production of sclareolide from sclareol and/or abienol.

A full definition of the trivial names and abbreviations used in the following in conjunction with the accompanying numbers in round brackets is given in the Example section which shows the associated IUPAC name and the corresponding structural formula.

2. Statement of the Related Art

Ambroxan (7) is a valuable ambergris fragrance which is found in a metabolic secretion of the sperm whale (cf. Ullmanns Enzyklopädie der technischen Chemic, Vol. 20, pages 283, Weinheim 1981). In view of limited natural resources, the increasing demand for ambroxan has led in recent years to the development of processes by which ambroxan can be synthetically obtained from inexpensive raw materials. Sclareolide (6) in particular has proved to be an important ambroxan precursor so that the concern of many research groups has been to develop processes by which sclareolide can be synthesized from natural raw materials, more particularly sclareol (1).

According to U.S. Pat. No. 3,050,532, sclareol is first oxidized with potassium permanganate under alkaline reaction conditions to form the hydroxyketone (3) which, without further isolation, is converted with glacial acetic acid into the enolethers (4). The enolether is then oxidized either with potassium permanganate or with chromic acid. The oxidation product obtained is saponified and then cyclized to form sclareolide (6). Unfortunately, this process is attended by the disadvantage that the oxidation step is carried out with potassium permanganate which is ecologically unsafe, i.e. toxic. In addition, the $MnO_2$ (magnesium dioxide) formed therefrom is very difficult to filter off in the working-up phase.

Finally, German patent application DE 39 42 358 describes a process in which sclareol is first oxidatively degraded with hypochlorite salts in the presence of ruthenium salts to form the hydroxyketone (3) and/or the enolether (4), the intermediate product thus obtained and isolated is oxidized with peracids and/or peracid salts and, after saponification and acidic ring closure, is converted into sclareolide. This process gives sclareolide in a yield of around 65%, based on sclareol.

Accordingly, in view of the key position of ambroxan in the field of fragrances, there is a general need to develop improved syntheses. This demand extends in particular to improvements in individual process steps and to the development of alternative syntheses for the production of important intermediate products or precursors of ambroxan. Accordingly, the problem addressed by the present invention was to create better access to sclareolide starting out from sclareol and structurally closely related compounds.

DESCRIPTION OF THE INVENTION

According to the invention, the solution to this problem characterized in that sclareol (1) and abienol (2) is first reacted with 10.5 to 25 times the molar quantity of an oxidizing agent in aqueous medium in the absence of an organic solvent and in the presence of a ruthenium catalyst and an emulsifier to form a crude product which, thereafter, is either converted in the presence of a base into the salt of 8α-hydroxy-11-carboxy-12,13,14,15,16-pentanorlabdane, hereinafter referred to as the hydroxy acid (5), and the hydroxy acid (5) is cyclized in acidic medium to form sclareolide or is subjected to an after-reaction at elevated temperature and subsequently distilled, the after-reaction optionally taking place in situ during the distillation phase.

Accordingly, the present invention relates to a process for the production of sclareolide in which sclareol and/or abienol is reacted with 10.5 to 25 times the molar quantity—based on sclareol and/or abienol—of an oxidizing agent in aqueous medium in the absence of an organic solvent and in the presence of a ruthenium catalyst and an emulsifier to form a crude product which, thereafter, is either (i) converted in the presence of a base into the salt of 8α-hydroxy-11-carboxy-12,13,14,15,16-pentanorlabdane which is then cyclized in acidic medium to form sclareolide or (ii) is subjected to an after-reaction at elevated temperature and subsequently distilled, the after-reaction optionally taking place in situ during the distillation phase.

The advantage of the process according to the invention is that only a single oxidation step is required and sclareol can be obtained in high yields. In addition, the oxidation step takes place in the absence of an organic solvent in contrast to the cited prior art. Finally, embodiment (ii) represents another advantageous form of the process in which certain process steps of embodiment (i) can be eliminated.

The oxidizing agent is used in a 10.5 to 25 molar excess, based on sclareol and/or abienol. A 12- to 16-fold excess is particularly preferred. Suitable oxidizing agents are, for example, peracids, hydrogen peroxide or alkali metal or alkaline earth metal hypochlorites. It has proved to be particularly favorable to use oxidizing agents in the form of aqueous solutions. A particularly suitable oxidizing agent is sodium hypochlorite.

There are no particular restrictions on the type of emulsifier used, although nonionic surfactants and in particular adducts of ethylene and/or propylene oxide with fatty alcohols or oxoalcohols have proved to be particularly favorable. It is of particular advantage to use an adduct of 20 moles of ethylene oxide with commercial tallow alcohol.

In order to shorten the reaction time, it has been found to be of advantage to expose the reaction mixture—which is present in the form of an aqueous dispersion—before the actual reaction to conditions which promote the formation of a particularly fine-particle dispersion. Such conditions include, for example, the application of ultrasound, the use of a high-speed shearing stirrer or a homogenizer, for example of the Supratron or Cavitron type.

The process is carried out at temperatures of 15° to 70° C. and preferably at temperatures of 20° to 50° C.

The ruthenium catalyst is used in a quantity of 0.1 to 5 mole-% and preferably in a quantity of 0.1 to 1.0 mole-%, based on sclareol and/or abienol. The ruthenium catalyst may consist both of elemental ruthenium, which may be used in the form of a powder or on a solid support, for example active carbon or aluminium oxide, and of hydrated ruthenium(IV) oxide ($RuO_2 \cdot nH_2O$) and ruthenium salts. Ruthenium trichloride ($RuCl_3$) has proved to be particularly suitable.

The process according to the invention is generally carried out as follows: sclareol and/or abienol and the emulsifier are initially introduced into water, an alkaline pH is if necessary adjusted by addition of alkali metal hydroxide and the ruthenium catalyst is added. The oxidizing agent is then introduced. A crude product mixture predominantly containing sclareolide and also secondary products is obtained. This crude product mixture is subsequently processed by one of the following variants:

(i) After the further addition of a base and heating, the secondary products are converted into the corresponding salt of the hydroxy acid (5); in this process, sclareolide is also converted by ring opening into the hydroxy acid (5). In a final step, the hydroxy acid (5) formed from the salt by acidification is cyclized in known manner by elimination of water to form sclareolide.

(ii) The crude product obtained in the oxidation step is heated under special conditions so that the secondary products mentioned can be converted into sclareolide without any additional processing steps. This may be done, for example, by initially heating the crude product for about 3 hours at temperatures of around 120° C.; the sclareolide is then distilled off under moderate conditions, for example using a thin-layer evaporator. On the other hand, conversion into sclareolide may be carried out in situ by distilling the crude product at temperatures which, on the one hand, are high enough to promote conversion of the secondary products into sclareolide, but which on the other hand are sufficiently moderate largely to avoid decomposition of the sclareolide. This may be achieved for example by distillation in a high vacuum at a temperature of around 140° C.

The following Examples are intended to illustrate the invention without limiting it in any way.

EXAMPLES

1. Trivial names/abbreviations

Sclareol (1):

8α,13-Dihydroxy-14,15-didehydrolabdane

Abienol (2):

8α-Hydroxy-12,13-didehydro-14,15-didehydrolabdane [the Z or E configuration may be present for the double bond between the atoms C-12 and C-13]

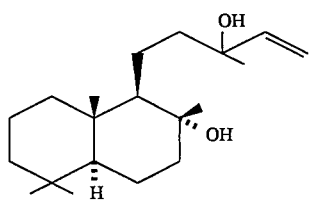

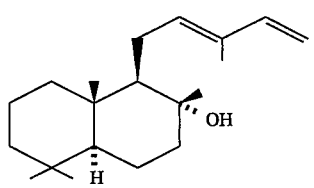

Hydroxyketone (3):

8α-Hydroxy-13-oxido-15,16-dinorlabdane

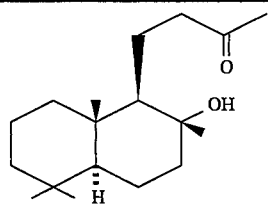

Enolether (4):

8α,13-Oxido-12,13-dehydro-15,16-dinorlabdane

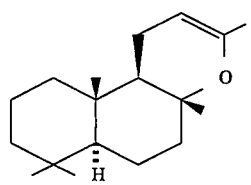

Hydroxy acid (5):

8α-Hydroxy-11-carboxy-12,13,14,15,16-pentanorlabdane

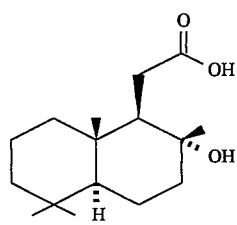

Sclareolide (6):

8α,12-Oxido-12-oxo-13,14,15,16-tetranorlabdane

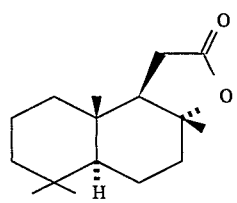

Ambroxan (7):

8α,12-Oxido-13,14,15,16-tetranorlabdane

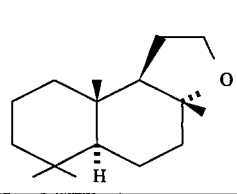

2. Production Examples

In the following, all percentages (except for yields) are percentages by weight.

Examples 1 and 2 illustrate variant (i) [oxidation of sclareol to crude sclareolide, subsequent conversion of the secondary products present therein into the hydroxy acid and subsequent cyclization of the hydroxy acid to sclareolide], Example 2 showing the advantages of using a particularly fine-particle dispersion.

Example 3 illustrates variant (ii) [oxidation of sclareol to crude sclareolide and its after-reaction in situ during the following distillation step].

EXAMPLE 1

(I) 62 g of sclareol and 1.9 g of an adduct of 20 moles of ethylene oxide with tallow fatty alcohol ("Dehydol TA 20", a product of Henkel KGaA, Düsseldorf) were introduced into 350 ml of water and heated with stirring to 80° C. The dispersion was left to cool to 35°–40° C., after which 0.83 g of ruthenium trichloride (25% solution, a product of Degussa AG) and 112.5 g of a 50% aqueous KOH solution were added. 1,862.5 g of a 13% aqueous sodium hypochlorite solution were then introduced with stirring over a period of 3 hours. After the NaOCl had been added, the reaction mixture was stirred overnight, cooling to room temperature in the process.

(II) For working up, the mixture was adjusted to a pH value of 1–2 with 150 ml of 40% sulfuric acid and the aqueous phase was separated off. The organic phase was taken up in 600 ml of toluene and washed twice with 250 ml of water.

(III) 27.5 g of a 50% NaOH solution and 2.8 g of tetrabutylammonium chloride were then added to the organic solution, after which the reaction mixture was stirred for 5 hours at 60° to 65° C. The reaction mixture was diluted with 500 ml of water, heated to 70° C. and the organic phase was separated off. The aqueous phase was adjusted to a pH value of 2 with 40% sulfuric acid and extracted with 300 ml of toluene.

(IV) The toluene solution was heated under reflux for 4–5 hours on a water separator. After the solvent had been distilled off, sclareolide was obtained in a yield of 72.6% of the theoretical.

EXAMPLE 2

Example 1 was repeated using 4 g of an adduct of 20 moles of ethylene oxide with sorbitan monooleate ("Disponil SMO 120", a product of Henkel KGaA, Düsseldorf) and 1.5 g of Dehydol TA 20 (see Example 1) as emulsifier. The dispersion formed was subsequently passed through a Cavitron which shortened the reaction time to 5 hours. Sclareolide was obtained in a yield of 75% of the theoretical.

EXAMPLE 3

Example 2 was repeated leaving out steps (III) and (IV). Instead, after acidification and phase separation, the organic residue was not taken up in toluene in step (II), but was directly distilled in a high vacuum (0.01 mbar) at 150° C. Sclareolide was obtained in a yield of 78% of the theoretical.

We claim:

1. A process for the production of sclareolide comprising the steps of: (1) providing an aqueous composition comprised of: (a) water; (b) sclareol, abienol, or a mixture of sclareol and abienol, (c) an effective amount of a ruthenium catalyst; and, (d) an emulsifying agent; (2) forming an aqueous alkaline composition by adding an alkali metal hydroxide to said aqueous composition; (3) reacting said aqueous alkaline composition with an oxidizing agent to form a crude product; (4) further reacting said crude product with base to form the salt of 8α-hydroxy-11-carboxy-12,13,14,15,16-pentanorlabdane; and (5) reacting said salt with acid to form sclareolide.

2. The process of claim 1 wherein said oxidizing agent is selected from the group consisting of a peracid, hydrogen peroxide, an alkali metal hypochlorite, and an alkaline earth metal hypochlorite.

3. The process of claim 1 wherein said oxidizing agent is sodium hypochlorite.

4. The process of claim 1 wherein said emulsifying agent is a nonionic surfactant.

5. The process of claim 4 wherein said nonionic surfactant is an adduct of 20 moles of ethylene oxide and commercial tallow alcohol.

6. The process of claim 1 wherein step (3) is carried out at a temperature of from about 15° C. to about 70° C.

7. The process of claim 1 wherein said ruthenium catalyst is used in an amount equal to from about 0.1 to about 5.0 mole percent based on the amount of sclareol or abienol.

8. The process of claim 1 wherein said ruthenium catalyst is $RuCl_3$.

9. The process of claim 7 wherein said ruthenium catalyst is $RuCl_3$.

10. The process of claim 1 wherein said aqueous alkaline composition is formed into a fine particle dispersion prior to step (3).

11. A process for the production of sclareolide comprising the steps of: (1) providing an aqueous composition comprised of: (a) water; (b) sclareol, abienol, or a mixture of sclareol and abienol, (c) an effective amount of a ruthenium catalyst; and, (d) an emulsifying agent; (2) forming an aqueous alkaline composition by adding an alkali metal hydroxide to said aqueous composition; (3) reacting said aqueous alkaline composition with an oxidizing agent to form a crude product; and (4) heating said crude product to form sclareolide.

12. The process of claim 11 wherein said oxidizing agent is selected from the group consisting of a peracid, hydrogen peroxide, an alkali metal hypochlorite, and an alkaline earth metal hypochlorite.

13. The process of claim 11 wherein said oxidizing agent is sodium hypochlorite.

14. The process of claim 11 wherein said emulsifying agent is a nonionic surfactant.

15. The process of claim 14 wherein said nonionic suffactant is an adduct of 20 moles of ethylene oxide and commercial tallow alcohol.

16. The process of claim 11 wherein step (3) is carried out at a temperature of from about 15° C. to about 70° C.

17. The process of claim 11 wherein said ruthenium catalyst is used in an amount equal to from about 0.1 to about 5.0 mole percent based on the amount of sclareol or abienol.

18. The process of claim 11 wherein said ruthenium catalyst is $RuCl_3$.

19. The process of claim 17 wherein said ruthenium catalyst is $RuCl_3$.

20. The process of claim 11 wherein said aqueous alkaline composition is formed into a fine particle dispersion prior to step (3).

* * * * *